United States Patent
Roller et al.

(10) Patent No.: US 8,795,591 B2
(45) Date of Patent: Aug. 5, 2014

(54) DUAL OUTLET OXYGENATOR FOR TREATING BLOOD IN AN EXTRACORPOREAL BLOOD CIRCUIT

(75) Inventors: Stephen Roller, Minneapolis, MN (US); Christopher Plott, St. Paul, MN (US); Alford McLevish, Maple Grove, MN (US); Gregory Hake, Otsego, MN (US); Brian Steffens, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 39 days.

(21) Appl. No.: 13/397,446

(22) Filed: Feb. 15, 2012

(65) Prior Publication Data

US 2013/0209314 A1 Aug. 15, 2013
US 2014/0050617 A9 Feb. 20, 2014

Related U.S. Application Data

(63) Continuation-in-part of application No. 13/015,363, filed on Jan. 27, 2011, now Pat. No. 8,518,259.

(51) Int. Cl.
*A61M 1/00* (2006.01)
*A61M 1/16* (2006.01)
*A61M 1/36* (2006.01)

(52) U.S. Cl.
CPC ............... *A61M 1/1698* (2013.01); *A61M 1/36* (2013.01)
USPC .............. 422/46; 422/45; 604/6.13; 604/6.14

(58) Field of Classification Search
CPC ... A61M 1/1678; A61M 1/1698; A61M 1/32; A61M 1/36; A61M 1/3666
USPC .............................. 604/6.13–6.14; 422/44–48
See application file for complete search history.

(56) References Cited

U.S. PATENT DOCUMENTS

| | | | |
|---|---|---|---|
| 5,445,613 A | 8/1995 | Orth | |
| 5,733,398 A | 3/1998 | Carson et al. | |
| 5,817,278 A * | 10/1998 | Fini et al. ..................... | 422/45 |
| RE36,125 E | 3/1999 | Haworth | |
| 5,906,741 A | 5/1999 | Elgas et al. | |
| 6,004,511 A | 12/1999 | Biscegli | |
| 6,302,860 B1 | 10/2001 | Gremel et al. | |
| 6,495,101 B1 | 12/2002 | Yokoyama et al. | |
| 6,689,315 B2 | 2/2004 | Linker et al. | |

(Continued)

FOREIGN PATENT DOCUMENTS

| | | |
|---|---|---|
| EP | 0713709 | 5/1996 |
| EP | 2335752 | 6/2011 |
| WO | WO97/33636 | 9/1997 |

*Primary Examiner* — Philip R Wiest
*Assistant Examiner* — Benjamin Klein (57) ABSTRACT

An apparatus for oxygenating blood including a housing and an oxygenator bundle. The housing defines a primary chamber, a blood inlet port open to the primary chamber, and a blood outlet region. The outlet region includes a blood outlet port, an outlet chamber open to the outlet port, and a partition. The partition establishes spaced apart, first and second passageways from the primary chamber to the outlet chamber. The oxygenator bundle is disposed within the primary chamber. A blood flow path is formed from the blood inlet port, through the oxygenator bundle and to the blood outlet port, and includes first and second outlet flow paths within the outlet chamber via the first and second passageways, respectively. The first and second outlet blood flow paths merge at the blood outlet port. A dual port blood outlet is created, increasing mixing of blood immediately upstream of the outlet port.

20 Claims, 10 Drawing Sheets

(56) References Cited

U.S. PATENT DOCUMENTS

| | | |
|---|---|---|
| 6,723,283 B2 | 4/2004 | Ghelli et al. |
| 6,773,670 B2 | 8/2004 | Stringer et al. |
| 7,022,099 B2 | 4/2006 | Litzie et al. |
| 7,131,966 B1 | 11/2006 | Tamari |
| 7,485,260 B2 * | 2/2009 | Tamari ........................... 422/44 |
| 7,871,566 B2 * | 1/2011 | Strauss et al. .................. 422/45 |
| 2002/0039543 A1 | 4/2002 | Ikeda et al. |
| 2005/0118059 A1 | 6/2005 | Olsen et al. |
| 2006/0089586 A1 * | 4/2006 | Kaus et al. .................... 604/4.01 |
| 2007/0166190 A1 | 7/2007 | Ogihara et al. |
| 2010/0272604 A1 | 10/2010 | Carpenter et al. |
| 2010/0272607 A1 * | 10/2010 | Carpenter et al. ............... 422/46 |
| 2010/0274170 A1 | 10/2010 | Carpenter |
| 2012/0193289 A1 * | 8/2012 | Cloutier et al. ............... 210/646 |

\* cited by examiner

DUAL OUTLET OXYGENATOR FOR TREATING BLOOD IN AN EXTRACORPOREAL BLOOD CIRCUIT

BACKGROUND

The present disclosure relates to extracorporeal blood circuit devices and related methods of use. More particularly, it relates to oxygenator devices (or combination devices including an oxygenator) for oxygenating blood in an extracorporeal blood circuit with improved outlet blood sampling accuracy.

An extracorporeal blood circuit is commonly used during cardiopulmonary bypass to withdraw blood from the venous portion of the patient's circulation system (via a venous cannula) and return the blood to the arterial portion (via an arterial cannula). The extracorporeal blood circuit typically includes a venous drainage line, a venous blood reservoir, a blood pump, an oxygenator, a heat exchanger, one or more filters, and blood transporting tubing, ports, and connection pieces interconnecting the components. Oftentimes, two or more components can be combined into a single device, such as a combination oxygenator and heat exchanger.

Blood oxygenators are disposable components of extracorporeal circuits and are used to oxygenate blood. In general terms, the oxygenator takes over, either partially or completely, the normal gas exchange function of the patient's lungs. The oxygenator conventionally employs a microporous membrane or bundle comprised of thousands of microporous or semipermeable hollow fibers. Blood flow is directed around the outside surfaces of hollow fibers. Concurrently, an oxygen-rich gas mixture is passed through the fiber lumens. Due to the relatively high concentration of carbon dioxide in the blood arriving from the patient, carbon dioxide is transferred from the blood, diffusing across the microporous fibers and into the passing stream of oxygenating gas. At the same time, oxygen is transferred from the oxygenating gas, diffusing across the fibers and into the blood. The oxygen content of the blood is thereby raised, and the carbon dioxide content is reduced.

After the blood has flowed around the fibers of the oxygenator bundle it must be routed outside the oxygenator housing via a blood outlet port. The perfusionist often desires to monitor various parameters of the blood as it exits the oxygenator. To meet this need, many available oxygenators incorporate one or more sampling or auxiliary ports at the blood outlet port and through which samples can be taken and/or other information obtained. For example, blood oxygenators can incorporate a sampling port for obtaining samples of the oxygenated blood (e.g., for blood gas analysis) and/or a monitoring port through which a temperature monitoring probe (or other device) can interface with the blood.

Because the sampling ports are provided along the blood outlet port, the blood flow path immediately upstream of the blood outlet port is of interest. Many currently available blood oxygenators (including oxygenators with an integrated heat exchanger) incorporate a generally cylindrically-shaped outer housing or case, with the blood outlet port being located at a side of the case. With this construction, blood flow through the oxygenator membrane is directed along the outer housing (and elsewhere within the case) to a single opening into the blood outlet port. This single opening port design is essentially an industry standard, and is conventionally understood as contributing to a low as possible prime volume attribute of the oxygenator. While well-accepted, the single opening blood outlet port design may limit the accuracy of blood-related parameters sensed or sampled at the blood outlet port.

In light of the above, a need exists for improved oxygenator designs that improve the accuracy of sensed or sampled blood-related parameters at the blood outlet port.

SUMMARY

Some aspects in accordance with principles of the present disclosure relate to an apparatus for oxygenating blood as part of an extracorporeal circuit. The apparatus includes a housing and an oxygenator bundle. The housing defines a primary chamber, a blood inlet port, and a blood outlet region. The blood inlet port is fluidly open to the primary chamber. The blood outlet region includes a blood outlet port, an outlet chamber, and a partition. The outlet chamber is fluidly open to the blood outlet port. The partition establishes spaced apart, first and second passageways from the primary chamber to the outlet chamber. Finally, the oxygenator bundle is disposed within the primary chamber and includes a plurality of gas exchange elements. With this construction, the apparatus establishes a blood flow path from the blood inlet port, through the oxygenator bundle and to the blood outlet port. In this regard, the blood flow path includes first and second outlet blood flow paths within the outlet chamber via the first and second passageways, respectively. The first and second outlet blood flow paths merge at the blood outlet port. A dual port blood outlet region is effectively created, increasing mixing of blood immediately upstream of the blood outlet port. Due to this elevated mixing, measurements or samples taken at the blood outlet port have increased accuracy while maintaining low hemolysis and prime volume. Further, a more even flow distribution through the oxygenator bundle can be provided. In some embodiments, the apparatus further includes a heat exchanger core disposed within the primary chamber. In other embodiments, the blood outlet port is located longitudinally above a terminal end of the partition. In yet other alternative embodiments, an air purge port and purge line are provided with the apparatus, along with a clamping mechanism and an optional bubble detector. The bubble detector detects presence of air in blood delivered to the apparatus, and the clamping mechanism is operated to selectively open and close the purge line based upon information from the bubble detector.

Other aspects in accordance with principles of the present disclosure relate to a method of operating an oxygenator apparatus for oxygenating blood within an extracorporeal circuit. The method includes fluidly connecting the blood inlet and outlet ports of the apparatus described above into an extracorporeal circuit. Blood from the patient is delivered to the blood inlet port and is oxygenated when passing through the oxygenator bundle. In this regard, the delivered blood flows from the inlet port, through the oxygenator bundle and to the blood outlet port, including the partition dividing blood flow from the oxygenator bundle into first and second outlet blood flow paths that merge at the blood outlet port.

DETAILED DESCRIPTION

Figure 1A:
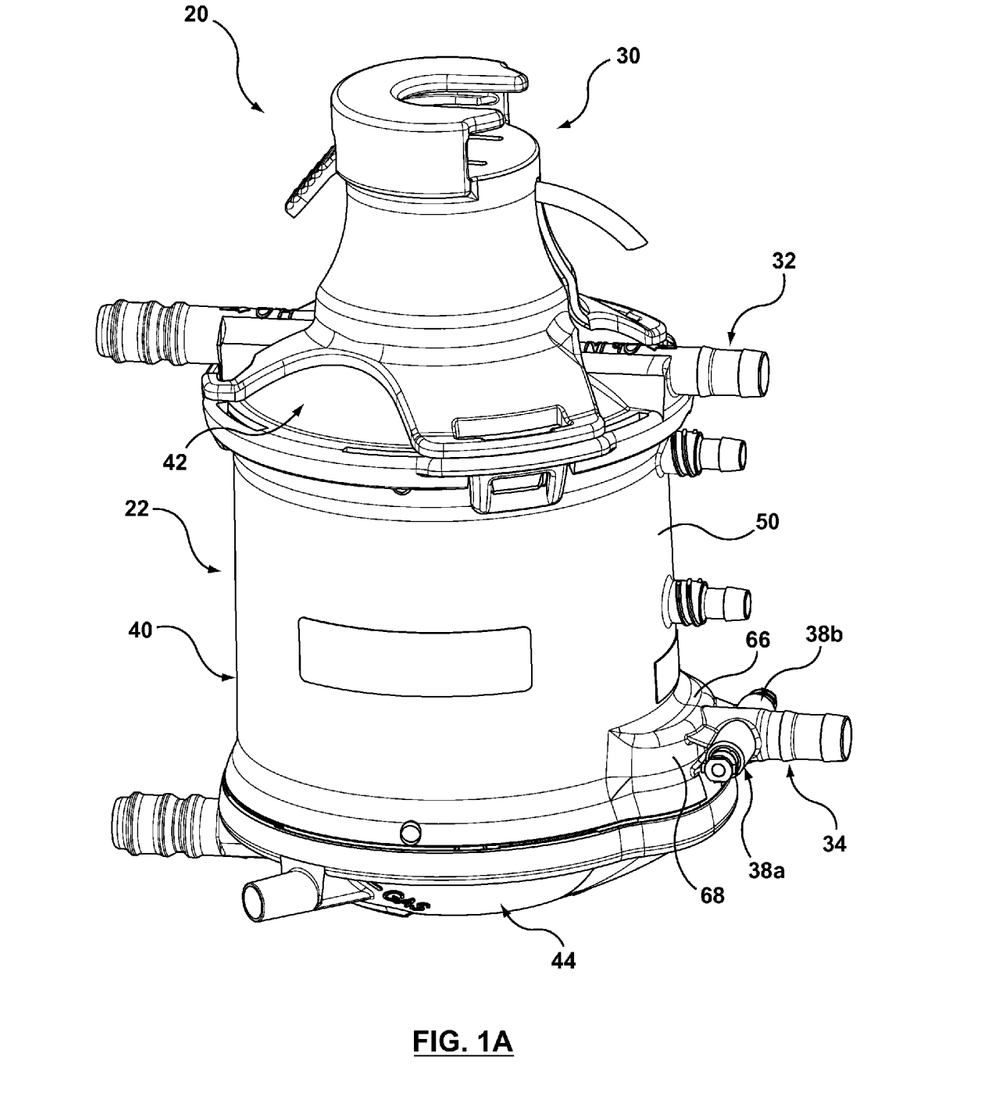
FIG. 1A is a perspective view of an apparatus for oxygenating blood in accordance with principles of the present disclosure.
Figure 1B:
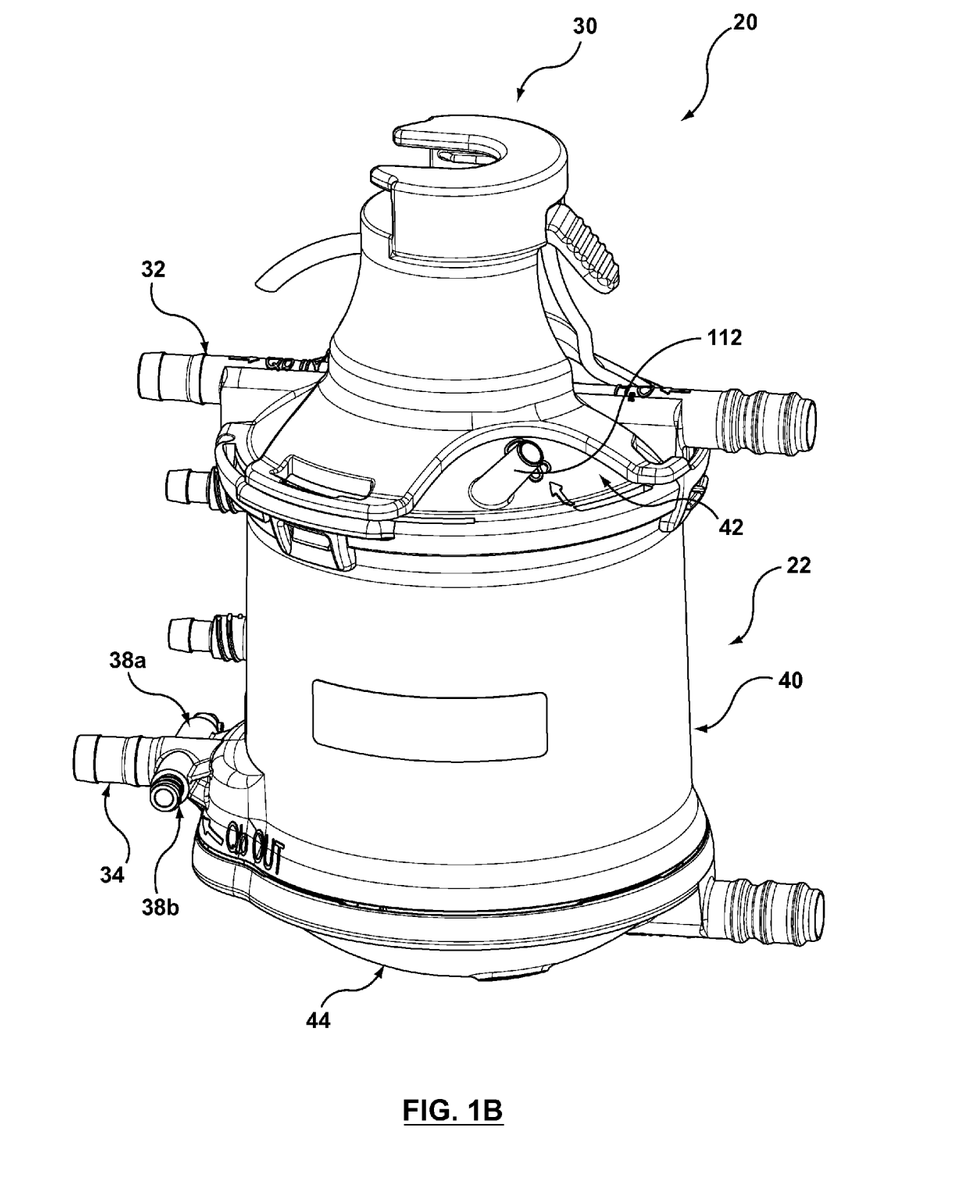
FIG. 1B is an opposite side perspective view of the apparatus of FIG. 1A.
Figure 2:
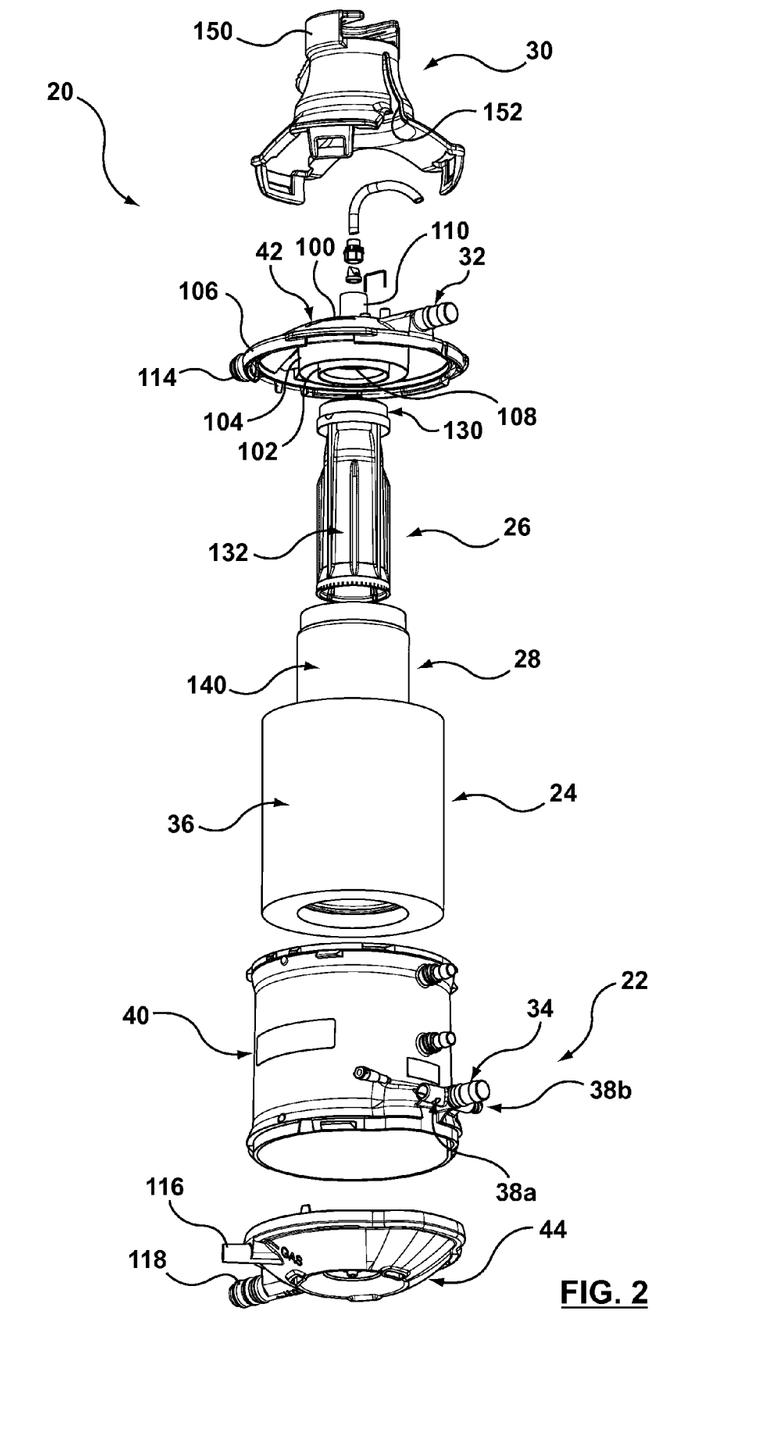
FIG. 2 is an exploded, perspective view of the apparatus of FIG. 1A.

One embodiment of an apparatus 20 in accordance with principles of the present disclosure and useful for treating blood in an extracorporeal blood circuit is shown in FIGS. 1A-2. The apparatus 20 includes a housing 22 and an oxygenator 24 (referenced generally). The apparatus 20 optionally includes one or more additional components, such as a manifold body 26, a heat exchanger 28 (referenced generally) and/or an auxiliary mounting bracket 30. Details on the various components are provided below. In general terms, however, the housing 22 provides or maintains a blood inlet port 32 and a blood outlet port 34. A blood flow path is defined from the blood inlet port 32 to the blood outlet port 34, with blood oxygenation occurring as the blood interfaces with an oxygenator bundle 36 of the oxygenator 24. Where provided, the heat exchanger 28 can effectuate temperature control of the blood as well. Regardless, one or more sampling ports 38a, 38b are provided along the blood outlet port 34 and through which samples or other testing parameters associated with the blood exiting the apparatus 20 can be obtained. In this regard, the apparatus 20, and in particular the housing 22, incorporates various features immediately upstream of the blood outlet port 34 that provide an elongated blood flow travel path (as compared to conventional designs), promoting mixing of the blood and increased accuracy of samples taken at the sampling ports 38a, 38b.

The housing 20 can assume a variety of forms and in some constructions is formed of two or more components that are separately formed and subsequently assembled to one another. For example, the housing 20 can include a central case 40, a first or upper end cap 42, and a second or lower cap 44. The end caps 42, 44 are configured for assembly to opposing ends of the case 40 as shown. In other constructions, the central case 40 is integrally formed with one or both of the end caps 42, 44. The housing 22 components can be made of a transparent medical grade material, such as a transparent polycarbonate, so that a user is able to observe the flow of blood through the apparatus 20.

Figure 3A:
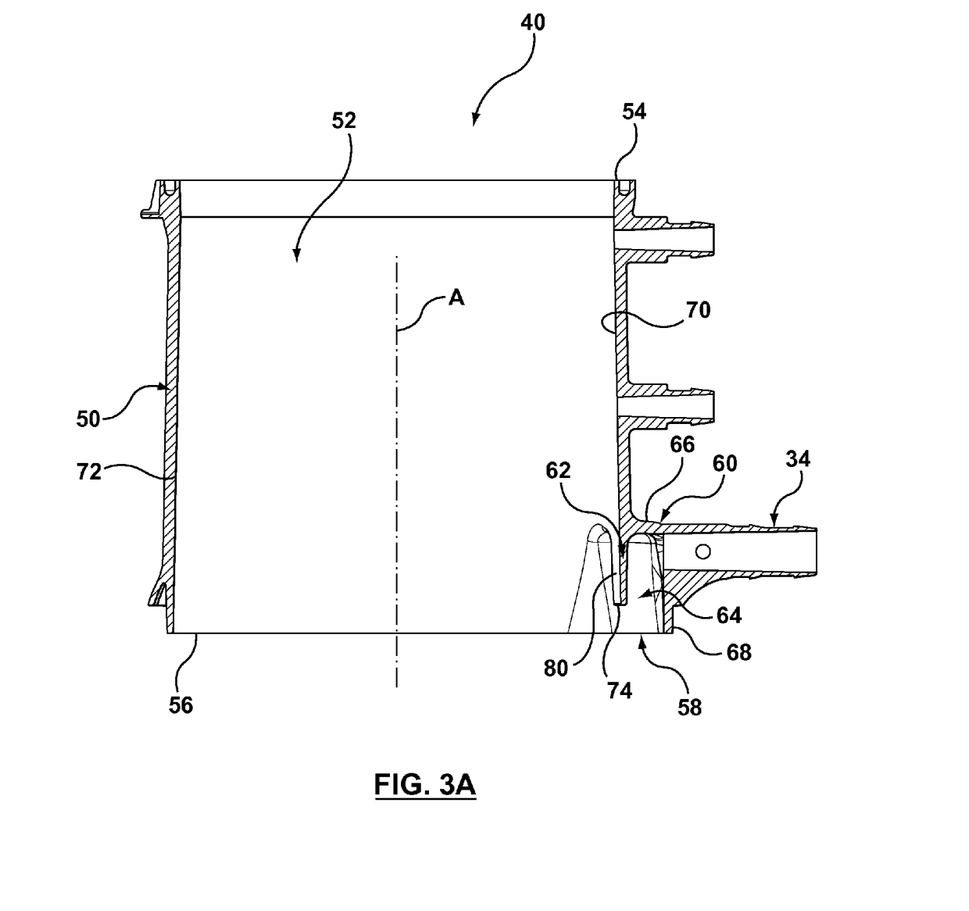
FIG. 3A is a longitudinal cross-sectional view of a housing case component of the apparatus of FIG. 1A.

The case 40 includes an outer side wall 50 that forms a primary chamber 52 as best shown in FIG. 3A. Longitudinal extension of the side wall 50 between opposing first and second ends 54, 56 defines a central axis A, with the primary chamber 52 being "closed" upon final assembly of the case 40 with the end caps 42, 44 (FIG. 2). The primary chamber 52 is sized to receive various blood treatment components (e.g., the oxygenator bundle 36 of FIG. 2) as described below. In addition, the case 40 forms or defines a blood outlet region 58.

The blood outlet region 58 includes an auxiliary wall 60 and a partition 62 that combine to define an outlet chamber 64. The outlet chamber 64 is located radially outwardly of the primary chamber 52 (relative to the central axis A), and is partially fluidly separated from the primary chamber 52 by the partition 62. The auxiliary wall 60 represents, in some constructions, a deviation from the otherwise substantially cylindrical shape or geometry of the side wall 50, and can be designated as having an upper portion 66 and a side portion 68. The upper portion 66 projects radially outwardly from the side wall 50. Relative to the longitudinal cross-section of FIG. 3A, the side portion 68 extends downwardly from the upper portion 66, terminating at the second end 56 (it will be understood that the side portion 68 is also connected to, and extends from, the side wall 50 as more fully illustrated in FIG. 1A). The blood outlet port 34 is connected to (or formed by) the side portion 68, and is fluidly open to the outlet chamber 64.

Figure 4:
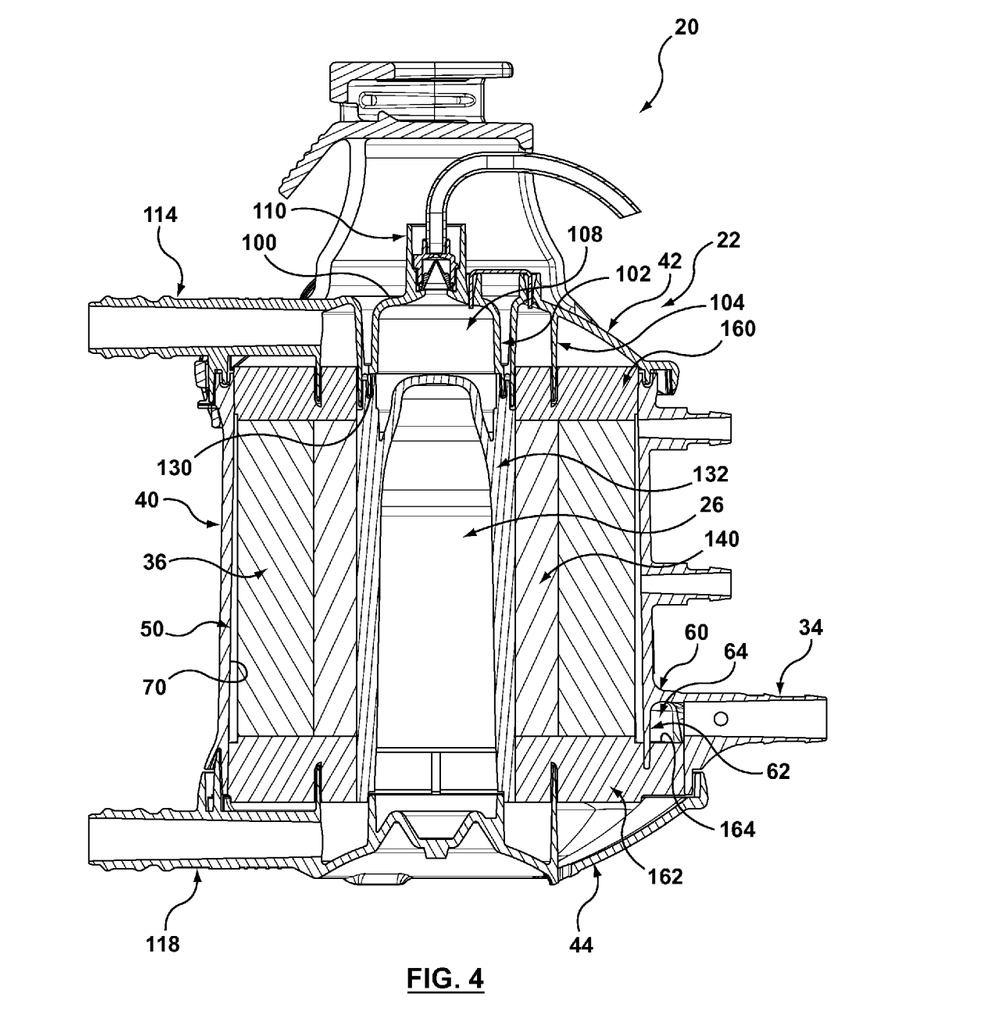
FIG. 4 is a cross-sectional view of the apparatus of FIG. 1A.

With continued reference to the longitudinal cross-section of FIG. 3A, the partition 62 is located generally opposite the side portion 68, and can be designated as a continuation of a shape of the side wall 50 in some constructions. By way of explanation, the side wall 50 has an inner surface 70 that is substantially parallel (e.g., within 10% of a truly parallel relationship) with the central axis A in extension between the first and second ends 54, 56. At a location (identified generally at 72) opposite the blood outlet region 58, as well as at as other locations except for the blood outlet region 58, this substantially parallel relationship continues to the second end 56. The upper portion 66 of the auxiliary wall 60 deviates from the substantially parallel relationship, projecting radially outwardly. The partition 62, in some embodiments, is a continuation of the substantially parallel arrangement, extending from the side wall 50, at the point of intersection with the upper portion 66, toward the second end 56 in a substantially parallel fashion with the central axis A. In some constructions, a terminal end 74 of the partition 62 is optionally off-set from the second end 56 (i.e., relative to the upright orientation of FIG. 3A, the terminal end 74 is spaced longitudinally above the side wall second end 56), all though in other embodiments, the partition terminal end 74 can extend beyond the position reflected in FIG. 3A. Further, the blood outlet port 34 is longitudinally off-set from the terminal end 74 in a direction opposite the side wall second end 56 (i.e., relative to the upright orientation of FIG. 3A, the blood outlet port 34 is longitudinally above the partition terminal end 74). Alternatively, the blood outlet port 34 can be positioned at different locations relative to an upright orientation of the apparatus 20 and the partition terminal end 74 need not be "below" the blood outlet port 34. Additionally, the side wall 50 and/or the partition 62 do not exhibit the above-described substantially parallel relationship in other embodiments. Regardless, the auxiliary wall 60 and the partition 62 define several boundaries of the outlet chamber 64, and locate the blood outlet port 34 along a fluid flow path apart from (but in fluid communication with) the primary chamber 52.

Figure 3B:
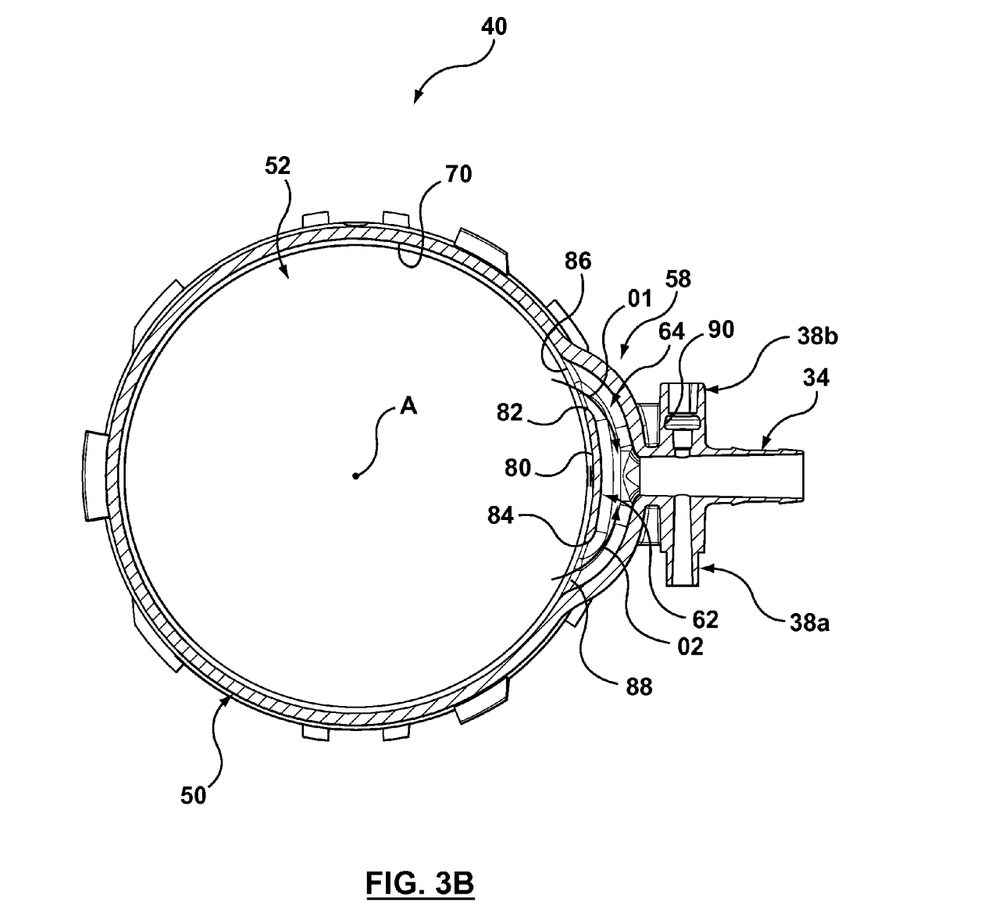
FIG. 3B is a transverse cross-sectional view of the housing case component of FIG. 3A.

The radially off-set arrangement of the outlet chamber 64 and the blood outlet port 34 relative to the primary chamber 52 is further reflected in FIG. 3B. As shown, in some embodiments, a curvature or shape of an inner face 80 of the partition 62 substantially corresponds with that defined by the inner surface 70 of the side wall 50. For example, relative to the central axis A, a radius of the partition inner face 80 approximates a radius of the side wall inner surface 70. In other embodiments, however, the partition 62 can define a shape or radius of curvature differing from that of the side wall 50. Regardless, the partition 62 defines or terminates at opposing side edges 82, 84 in some embodiments. Relative to the circumferential shape of the side wall 50 (in the transverse cross-sectional view of FIG. 3B), the side edges 82, 84 are circumferentially spaced from the side wall 50, establishing first and second passageways or openings 86, 88, respectively, between the primary and outlet chambers 52, 64. The passageways or openings 86, 88 can be defined in a variety of other fashions, and the present disclosure is not limited to a spacing between the opposing side edges 82, 84 of the partition 62 and the side wall 50. For example, the partition can have a more continuous extension across the side wall 50, with the passageways 86, 88 being integrally formed in the partition 62. The passageways 86, 88 are circumferentially spaced from one another, and in some constructions are equidistantly spaced from the blood outlet port 34 (although in other embodiments, the blood outlet port 34 can be spatially closer to one of the passageways 86 or 88). Liquid fluid flow can occur from the primary chamber 52 to the outlet chamber 64 (and thus to the blood outlet port 34) via both of the first and second passageways 86, 88. Thus, the blood outlet region 58 establishes first and second outlet blood flow paths (designated by arrows "01" and "02" in FIG. 3B). As shown, the outlet blood flow paths 01, 02 merge at the blood outlet port 34. In effect, the blood outlet region 58 provides a dual outlet to the blood outlet port 34 via the first and second passageways 86, 88 and the first and second outlet blood flow paths 01, 02.

FIG. 3B illustrates the auxiliary sampling ports 38$a$, 38$b$ in greater detail. The sampling ports 38$a$, 38$b$ can assume a variety forms appropriate for a desired interface with blood flowing through the blood outlet port 34. For example, the first sampling port 38$a$ can be configured to facilitate withdrawal of a blood sample from the blood outlet port 34 (e.g., for blood gas analysis), and thus is fluidly open to the blood outlet port 34. The second sampling port 38$b$ can be configured to maintain a separate device, for example a temperature monitoring probe, and can incorporate features 90 for maintaining a sleeve (not shown) that interfaces with the temperature probe. Where provided, the sleeve prevents blood from flowing into the second sampling port 38$b$ and contacting the temperature probe. Additional auxiliary sampling ports can be provided, or one of the illustrated sampling ports 38$a$ or 38$b$ can be modified or even eliminated in other embodiments. Regardless, one or more of the sampling ports 38$a$, 38$b$ can be fluidly open to the blood outlet port 34, and thus interface with blood flow following merging (and mixing) in the outlet chamber 64 (absent a separate structure, such as the temperature probe sleeve mentioned above, that otherwise seals the sampling port).

Returning to FIG. 2, the first end cap 42 can incorporate various features, and generally includes a top wall 100, a first ring 102, a second ring 104 and a rim 106. The first ring 102 extends from the top wall 100, and defines a de-aering chamber 108 described in greater detail below. The blood inlet port 32 extends from the top wall 100 and is fluidly open to the de-aering chamber 108. Further, the top wall 100 forms an air purge port 110 that is also fluidly open to the de-aering chamber 108. The second ring 104 is radially outside of the first ring 102, and is constructed to receive a portion of the heat exchanger 28. The rim 106 forms an outer perimeter of the first end cap 42, and is configured for assembly to the case 40. Finally, the first end cap 42 can form or maintain additional components, such as an oxygenator inlet port 112 (visible in FIG. 1B) and an optional heat exchanger inlet port 114 (with embodiments in which the apparatus 20 includes the heat exchanger 28).

The second end cap 44 can also assume various forms, and is generally constructed for assembly to the central case 40. Further, the second end cap 44 can form or maintain one or more ports, such as, for example, an oxygenator outlet port 116 and an optional heat exchanger outlet port 118 (with embodiment in which the apparatus 20 includes the heat exchanger 28). Further, a geometry of the second end cap 44 can mimic the outwardly protruding shape of the auxiliary wall 60 formed by the case 40.

The manifold body 26 is configured for assembly within the housing 22, arranged co-axially with the central axis A (FIG. 3A) in some embodiments. The manifold body 26 is generally constructed to facilitate blood flow from the blood inlet port 32 toward the oxygenator bundle 36 as described below, and can incorporate various features such as a hub structure 130 and a base 132. The hub structure 130 facilitates assembly of the manifold body 26 to the first end cap 42, and effectuates desired volume displacement in combination with various surface features of the base 132 in some embodiments. The base 132, in turn, promotes smooth flow of blood from a region of the hub structure 130 in a generally radially outward fashion toward the oxygenator bundle 36. In this regard, the manifold body 26 can incorporate other features apart from those shown, and may or may not include the hub structure 130 and/or the base 132 as illustrated.

The oxygenator 24 includes the oxygenator bundle 36 as mentioned above. The bundle 36 includes a plurality of gas exchange elements (not individually shown). The bundle or plurality of hollow fibers are used for gas exchange and are made of semi-permeable membrane including micropores. In some embodiments, the gas exchange elements are hollow polypropylene-based fibers, but other materials are also contemplated by the present disclosure. Any suitable microporous hollow fiber may be used as the gas exchange elements of the oxygenator bundle 36. With embodiments in which the apparatus 20 includes the heat exchanger 28, the oxygenator bundle 36 is arranged around a heat transfer core 140 (described in greater detail below). In other constructions, the oxygenator bundle 36 can be arranged directly on the manifold body 26 or a separately-provided mandrel. Even further, the hollow fibers of the oxygenator bundle 36 can be wound (e.g., helically wound) directly onto the heat transfer core 140, the manifold body 26, or the separate mandrel, as described, for example, in U.S. Pat. No. 5,346,612 the entire teachings of which are incorporated herein by reference. As known to those of skill in the art, the winding angle and/or tension during the winding process can be manipulated to affect a variable packing fraction as desired. One example pattern of winding the fibers of the oxygenator bundle 36 is found in the Affinity™ oxygenator available from Medtronic, Inc., of Minneapolis, Minn. Regardless of an exact construction, the oxygenator bundle 36 is sized and shaped for assembly within the housing 22 as described below, and the oxygenator 24 can include additional components (e.g., a potting compound) to effectuate sealed, fluid communication of the hollow fibers with the oxygenator inlet and outlet ports 112, 116.

An oxygen-containing gas medium is provided through the plurality of gas exchange elements of the oxygenator bundle 36. Certain gases are able to permeate the fibers. Carbon dioxide form the blood surrounding the fibers diffuses through the walls of the fibers and into the gas mixture. Similarly, oxygen from the gas mixture inside the fibers diffuses through the micropores into the blood. The gas mixture then has an elevated carbon dioxide content and preferably exits the fibers as it moves to the oxygenator outlet port 116. Although oxygen and carbon dioxide are preferably being exchanged, the present disclosure also contemplates that other gases may be desired to be transferred.

Any suitable gas supply system may be used with the oxygenator 24. For example, the gas supply system may include flow regulators, flow meters, a gas blender, an oxygen analyzer, a gas filter, and a moisture trap. Other alternative or additional components in the gas supply system can be included.

As mentioned above, the optional heat exchanger 28 includes the heat transfer core 140 comprised of a bundle or plurality of hollow heat transfer elements that may be fibers, tubes, capillaries, compartments, etc. (not shown individually). In some embodiments, the heat transfer elements comprise a thermally conductive polymer or metal. Various shapes of heat transfer elements are contemplated by the present disclosure. One exemplary material for the heat exchanger capillaries is polyethylene terephthalate, for example HEX PET™ heat exchange capillary. The HEX PET pre-made mat generally comprises two layers of hollow capillaries, with the two layers being angled with respect to one another (e.g., a 15 degree angle or bias from normal). Other materials are also envisioned. In general terms, the purpose of the heat transfer elements of the heat transfer core 140 is to transfer heat to or from the exchange fluid running there through to or from the blood that flows between the heat transfer elements.

The heat transfer elements of the heat transfer core 140 are located around the manifold body 26, and may be tightly wound or wrapped concentrically about the manifold body 26. Also, the heat transfer elements may be located such that there is minimal or no structural obstruction between the manifold body 26 and the heat exchanger core 140. Alternatively to the heat transfer elements actually being wound on the manifold body 26, the heat transfer core 140 can comprise heat transfer elements that are pre-arranged in a woven mat or fabric-like arrangement that is assembled over the manifold body 26.

The heat exchanger 28 may either heat or cool the blood flowing through the apparatus 20. Since hypothermia may be used during cardiac surgery (especially in infant and pediatric surgeries), to reduce oxygen demand, and since rapid re-warming of the blood can produce bubble emboli, the heat exchanger 28 is generally used to gradually re-warm blood and prevent emboli formation. The exchange or heat transfer fluid used in the heat exchanger 28 may comprise water or other suitable fluids. The heat exchanger 28 may incorporate hot and cold tap water that is run through the plurality of heat transfer elements. In some embodiments, however, a separate heater/cooler unit (not shown) with temperature-regulating controls is used to heat or cool the exchange fluid outside of the apparatus 20 as necessary to regulate the temperature of the blood flowing between the heat transfer elements as desired. As another alternative, a heat transfer means other than a fluid is possible. For example, thermoenergy may be supplied to the heat transfer elements rather than a fluid. The heat transfer core 140 is sized and shaped for assembly within the housing 22, and can incorporate bands and/or a potting compound (as known in the art) to effectuate sealed, fluid communication between opposing ends of the heat transfer elements and the heat exchanger inlet and outlet ports 114, 118.

Finally, the optional mounting bracket 30 is configured for assembly to the upper end cap 42, and provides one or more optional features. For example, the mounting bracket 30 can include a mounting clip 150 that facilitates releasable coupling with a separate perfusion stand (not shown), a tube management system 152, etc. The mounting bracket 30 can assume a variety of other forms not necessarily implicated by the drawings, and in other embodiments can be omitted.

Final assembly of the apparatus 20 is shown in FIG. 4, and includes the manifold body 26 mounted within the housing 22. The hub structure 130 is attached to the first ring 102 of the first end cap 42, with the de-aering chamber 108 being bounded by the top wall 100, the first ring 102 and the manifold body base 132. The heat transfer core 140 and the oxygenator bundle 36 are mounted within the primary chamber 52. For example, the heat transfer core 140 (where provided) is assembled about the manifold body 26, and is held between the first and second rings 102, 104 (as well as by the second end cap 44). The oxygenator bundle 36 is assembled over the heat transfer core 140, and has an outer diameter (or other dimension) selected to establish a small gap between the oxygenator bundle 36 and the inner surface 70 of the case side wall 50 in some embodiments. The oxygenator bundle 36 is further maintained by mounting to the first and second end caps 42, 44. Potting compounds 160, 162 are applied to the oxygenator bundle 36 and the heat transfer core 140 (where included). In some constructions, the second potting compound 162 is formed across an entirety of the housing 22 adjacent the second end cap 44, and encompasses a portion of the partition 62 (i.e., relative to the orientation of FIG. 4 the second potting compound 162 projects "above" the terminal end 74. With this construction, the second potting compound 162 forms a floor boundary 164 of the outlet chamber 64 (e.g., the outlet chamber 64 is bounded by the auxiliary wall 60, the partition 62 and the floor 164). Alternatively, one or more separate structures or bodies apart from the potting compound 162 can be employed to close the outlet chamber 64 relative to the partition end 74. For example, the partition 62 can extend to and abut the second end cap 44 upon final assembly. Assembly of the second end cap 44 to the case 40 closes the primary chamber 52.

With the above construction, an oxygenation gas flow path is established from the oxygenator inlet port 112 (FIG. 1B), through the hollow fibers of the oxygenator bundle 36, and to the oxygenator outlet port 116 (FIG. 1A). Similarly, a heat exchange medium flow path is established form the heat exchanger inlet port 114, through the fibers of the heat transfer core 140, and to the heat exchanger outlet port 118. An air purge flow path is established from the de-aering chamber 108 to the air purge port 110. Finally, a blood flow path is established from the blood inlet port 32 (FIG. 1A), to the manifold body 26, through the heat exchanger core 140, through the oxygenator bundle 36, to the blood outlet region 58, and then to the blood outlet port 34.

Figure 5A:
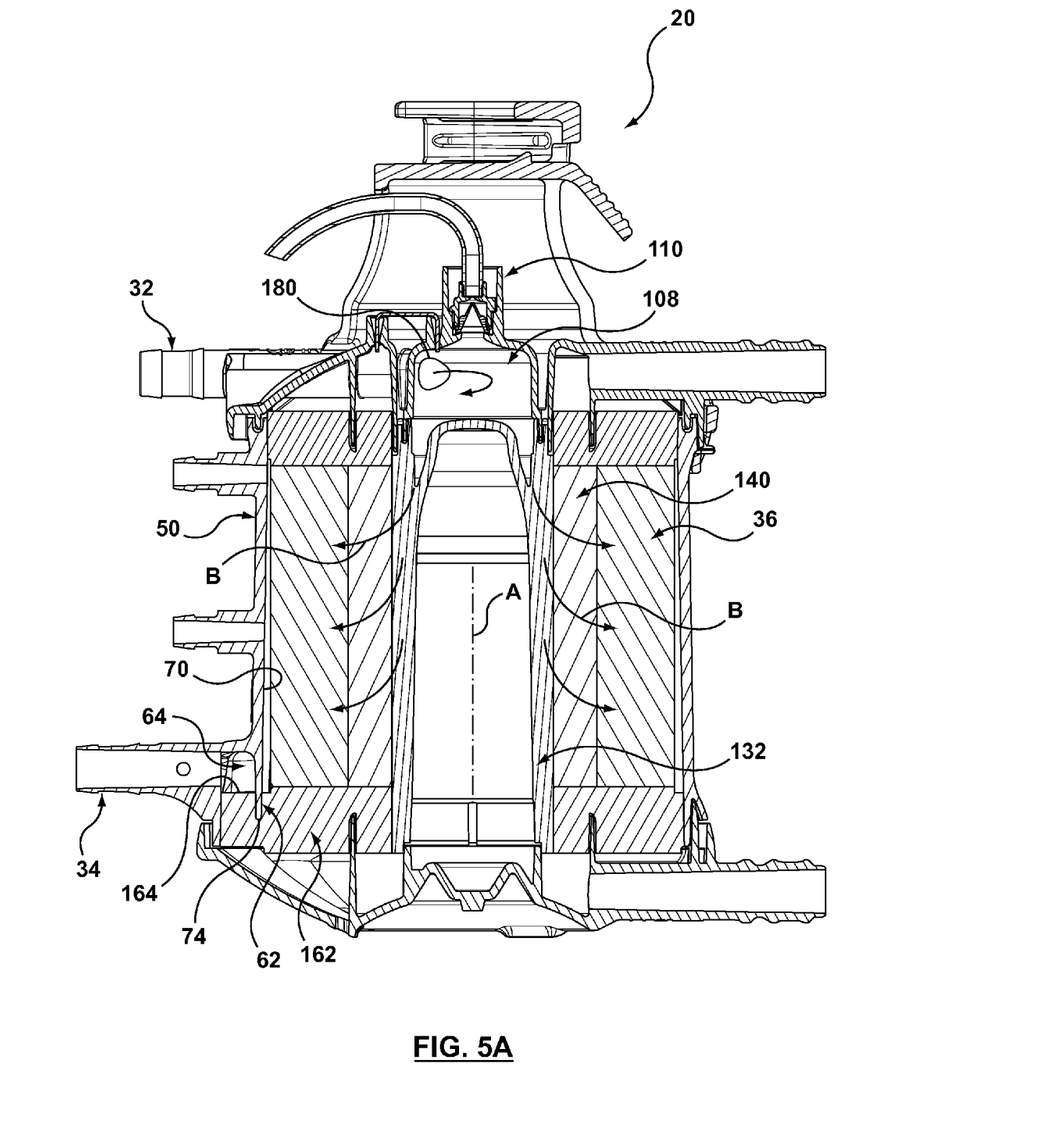
FIGS. 5A and 5B illustrate a blood flow path through the apparatus of FIG. 1A.

The blood flow path is shown by arrows "B" in FIG. 5A. Initially, the blood flow path optionally includes a rotational or vortex flow within the de-aering chamber 108 from the blood inlet port 32 via an aperture 180. As blood tangentially enters the de-aering chamber 108, a swirling motion (vortexing) is induced, creating a pressure differential in the chamber 108. This pressure differential separates gross air from the incoming blood in the form of air bubbles. Due to the centrifugal force of the vortex flow, the air bubbles are forced to the central axis A and are relieved from the apparatus via the air purge port 110. Thus, gross air removal (or de-aering) can occur prior to the blood encountering the heat transfer core 140 or the oxygenator bundle 36. In other embodiments of the present disclosure, however, the de-aering chamber 108 can have a wide variety of other forms, and can even be omitted.

Figure 5B:
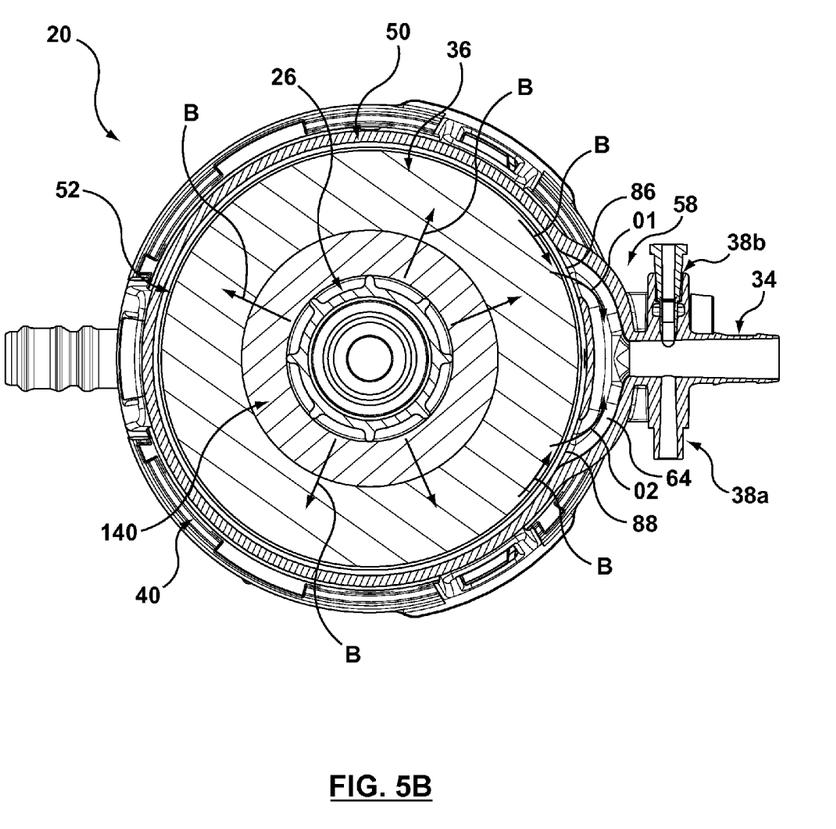

Blood flow from the de-aering chamber 108 is initially generally longitudinal along the manifold body base 132 and then transitions to a substantially radial direction (relative to the central axis A) to and through the heat exchanger core 140. A heat exchange fluid is forced through the heat exchange elements, effectuating transfer of heat with the blood in a desired direction. Substantially radial flow of the blood continues through the oxygenator bundle 36, continuing to the inner surface 70 of the case side wall 50. It will be understood that radial blood flow from the manifold body base 132 occurs in all directions, and that due to the substantially cylindrical shape of the case side wall 50, blood flow may be directed along the side wall inner surface 70 in a relatively circular fashion. As the primary chamber 52 fills with blood, the blood volume level is above the outlet chamber floor 164. As a result blood flow into the outlet chamber 58 occurs only through the passageways 86, 88 (hidden in the view of FIG. 5A). This occurrence is reflected in FIG. 5B, again by the blood flow path arrows B. The blood flow path B progresses from the primary chamber 52 (at least in part along the case side wall 50) to the first and second passageways 86, 88 of the blood outlet region 58. Because blood flow occurs in both circumferential directions (e.g., clockwise and counterclockwise relative to the orientation of FIG. 5B), the blood flow path B thus includes the first and second outlet blood flow paths 01, 02. Blood flow along the outlet flow paths 01, 02 continues, merging at the blood outlet port 34.

The dual outlet configuration provided by the blood outlet region 58 constructions of the present disclosure effectively elongates a flow length that the blood travels from the case 40 to the blood outlet port 34 as compared to conventional designs in which the blood outlet port is located directly at the primary chamber (and is effectively a single outlet port). As a point of reference, mixing occurs as the blood travels down a flow path. Therefore, the longer the path, the more mixing will take place. Further mixing occurs due to the merging of the two outlet blood flow paths 01, 02. This, in turn, beneficially increases the accuracy of measurements of blood samples (or other blood-related parameters) taken from the sampling ports 38a, 38b; the measurements will be taken from the more representative, well-mixed blood. The dual outlet configurations of the present disclosure also have the benefit of creating a more uniform flow through the oxygenator bundle 36. A more uniform flow creates a uniform residence time for the blood in the fiber bundle, thereby optimizing gas transfer through the apparatus 20.

Testing was performed to evaluate the accuracy of blood sample measurements at the blood outlet port as provided by the apparatuses of the present disclosure. A sample blood treatment apparatus in accordance with the present disclosure and akin to that shown in FIG. 2 was created (having the dual outlet design). A comparative example blood treatment device akin to FIG. 2 but with a conventional, single outlet design was also provided. Both the sample and comparative example apparatuses were subjected to testing in which blood was processed and oxygen transfer measurements taken at a sampling port provided at the corresponding blood outlet port. In particular, gas transfer testing was performed using a bovine blood model in accordance with FDA-specified guidance found in "Guidance for Cardiopulmonary Bypass Oxygenator 501(k) Submissions; Final Guidance for Industry and FDA Staff". Basically, blood and oxygen gas flow is provided through the blood treatment apparatus, and blood conditions are measured at the inlet, outlet and sampling port. From these conditions, gas transfer can be calculated for the blood outlet and sampling port and then compared to determine the accuracy of the measurement at the sampling port versus the outlet. It was surprisingly found that the measurements taken with the apparatus of the present disclosure were 10% more accurate than those taken with the conventional, single outlet device.

It will be understood that the blood outlet region 58 constructions of the present disclosure may increase the prime volume of the apparatus as compared to the conventional single or "straight" outlet design. However, testing has confirmed that this increase in prime volume is negligible (on the order of 1-2%).

Figure 6:
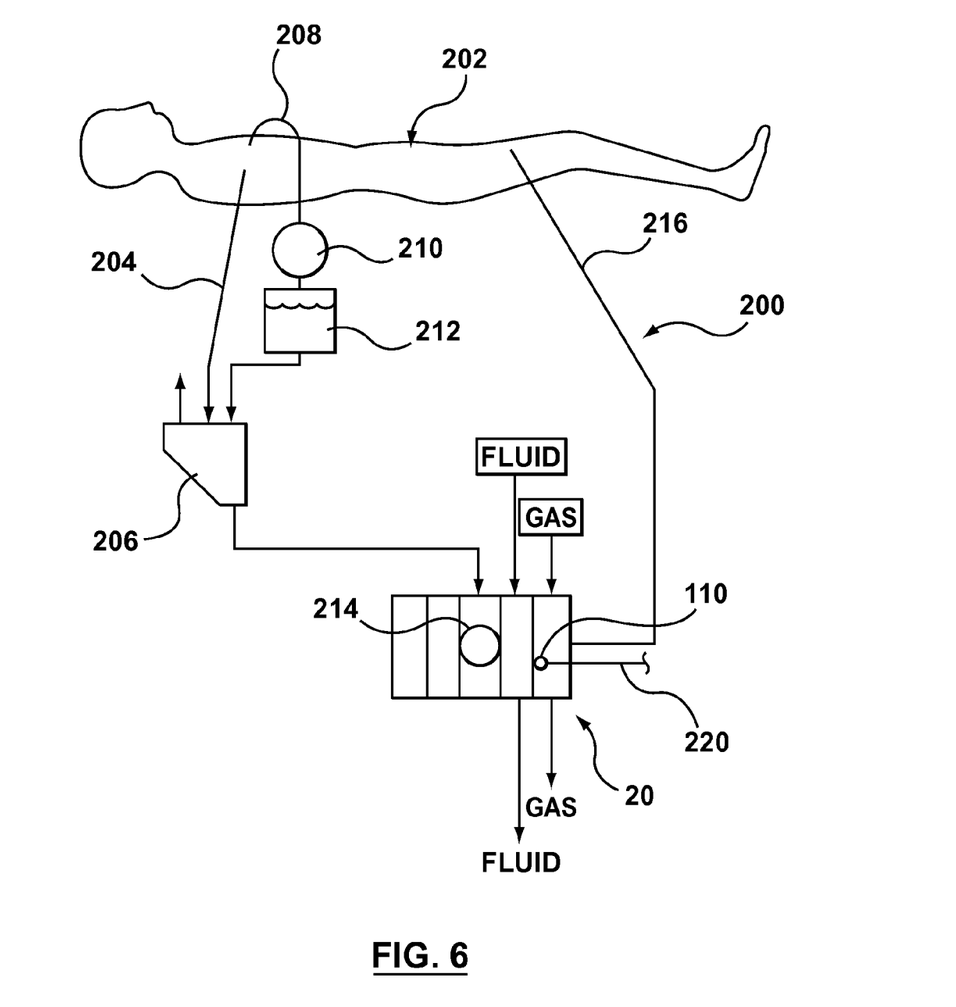
FIG. 6 is a schematic drawing of a cardiopulmonary bypass circuit including the apparatus of FIG. 1A.

The apparatus 20 of the present disclosure may be used or incorporated into any appropriate system or device in which blood is desired to be oxygenated (and, optionally, temperature controlled). One particular system is an electromechanical extracorporeal circulatory support system known as a cardiopulmonary bypass (CPB) system, commercially sold by Medtronic, Inc., of Minneapolis, Minn. under the trade name Performer-CPB System. Other systems are contemplated by the present disclosure. With this in mind, FIG. 6 provides an exemplary extracorporeal blood circuit 200 that includes the apparatus 20. The circuit 200 generally draws blood of a patient 202 during cardiovascular surgery through venous line 204. Venous blood drawn from the patient 202 is discharged into a venous reservoir 206. Cardiotomy blood and surgical field debris are aspirated by a suction device 208 and are pumped by a pump 210 into a cardiotomy reservoir 212. Once defoamed and filtered, the cardiotomy blood is also discharged into the venous reservoir 206. Alternatively, the function of the cardiotomy reservoir 212 may be integrated into the venous reservoir 206. In the venous reservoir 206, air entrapped in the venous blood rises to the surface of the blood and is vented to the atmosphere.

A pump 214 draws blood from the venous reservoir 206 and pumps it through the apparatus 20. Some exemplary types of pumps 214 include, but are not limited to, roller pumps and centrifugal pumps. The pump 214 may be external to the apparatus 20 as shown, or may alternatively be incorporated into the apparatus 20. As described above, the blood is de-aerated, temperature controlled, and oxygenated by the apparatus 20, and then returned to the patient 202 via an arterial line 216.

Figure 7:
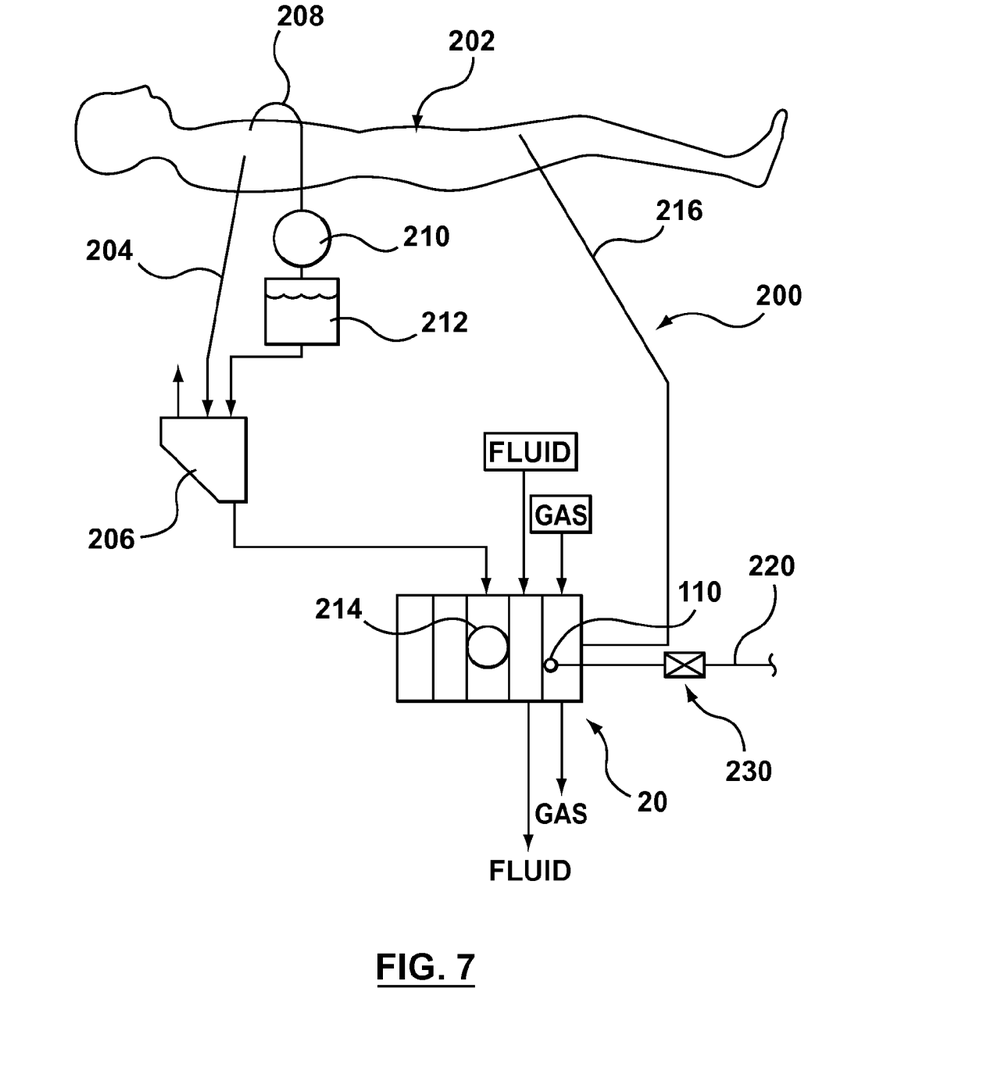
FIG. 7 is a schematic drawing of another cardiopulmonary bypass circuit including an apparatus for oxygenating blood and controlling air purging in accordance with principles of the present disclosure.

During operation of the apparatus 20 as part of the circuit 200, air is purged from apparatus 20 via the air purge port 110 (referenced generally in FIG. 6). In some embodiments, during normal operation this purge will consist solely of blood, which may detract from the total blood flow out of the apparatus 20. When air enters the apparatus 20, the inlet geometry forces the air out of the air purge port 110 and though an air purge line 220. In alternative embodiments of the present disclosure, and as reflected in FIG. 7, a clamping mechanism 230 (shown schematically) and a bubble detector 232 (shown schematically) are included. The clamping mechanism 230 is associated with the air purge line 220 and can assume a variety of forms appropriate for selectively opening and closing the air purge line 220. For example, the clamping mechanism 230 can be or can include an automated tubing clamp. In other embodiments, the clamping mechanism 230 can further include a controller that controls operation of the tubing clamp. The clamping mechanism 230, the controller, or the bubble detector 232 can be integrated into the apparatus 20. Regardless, the bubble detector 232 is of a type known in the art and is located along a blood inlet line 234 otherwise supplying blood to the blood inlet port 32 (referenced generally). With embodiments in which the clamping mechanism 230 includes a controller, the clamping mechanism controller can be electronically connected to the bubble detector 232, and programmed to operate the tubing clamp (or similar device) as a function of information signaled from the bubble detector 232. Alternatively, a user can monitor the bubble detector 232 and operate the clamping mechanism 230 based upon information from the bubble detector 232. Under normal operating conditions (i.e., no gross air in the blood as otherwise exhibited at the bubble detector 232), the clamping mechanism 230 is closed and prevents fluid flow through the air purge line 220. If air is introduced into the circuit 200, the bubble detector 232 will detect the air "upstream" of the apparatus 20; in response, the clamping mechanism 230 is operated (either automatically or manually) to open the air purge line 220. The air will then be allowed to purge from the apparatus 20 (and to the venous reservoir 206, for example). In some embodiments, the clamping mechanism controller can be programmed to automatically close the tubing clamp when no air is present (as otherwise indicated by the bubble detector 232). Alternatively, a user interface can be provided; the clamping mechanism controller interacts with the user interface in a manner requiring the perfusionist to acknowledge the presence of air (at the bubble detector 232) and take an affirmative action (e.g., press a button) to "rearm" the clamping mechanism 230 and close the tubing clamp. In yet other embodiments, the clamping mechanism 230 and the bubble detector 232 can be omitted.

The blood treatment apparatuses of the present disclosure provide a marked improvement over previous design. By incorporating the dual port blood outlet region, accuracy of temperature and blood gas measurements (or other data) taken at the blood outlet port is increased, more even flow distribution through the oxygenator bundle is achieved leading to increased gas transfer through the apparatus, and there is a minimal increase in prime volume. With alternative embodiments including the clamping mechanism and bubble detector, potential drawbacks associated with a continuous purge are minimized.

Although the present disclosure has been described with reference to preferred embodiments, workers skilled in the art will recognize that changes can be made in form and detail without departing from the spirit and scope of the present disclosure. For example, while the blood treatment apparatuses of the present disclosure have been described as including or providing heat exchange components, in other embodiments, the heat exchanger can be omitted. Conversely, the apparatuses of the present disclosure can incorporate additional blood treatment components, such as one or more layers of filter material.

What is claimed is:

1. An apparatus for oxygenating blood in an extracorporeal circuit, the apparatus comprising:
   a housing defining a primary chamber about a central longitudinal axis, a blood inlet port fluidly open to the primary chamber, and a blood outlet region, wherein the blood outlet region includes:
   a blood outlet port,
   an outlet chamber fluidly open to the blood outlet port,
   a partition separating the outlet chamber from the primary chamber and establishing spaced apart, first and second passageways from the primary chamber to the outlet chamber,
   wherein relative to a plane perpendicular to the central longitudinal axis and passing through the primary chamber and the outlet chamber, the outlet chamber and the partition each surrounds less than an entirety of the primary chamber; and
   an oxygenator bundle apart from the partition and disposed within the primary chamber, the oxygenator bundle including a plurality of gas exchange elements;
   wherein the apparatus establishes a blood flow path from the blood inlet port, through the oxygenator bundle, and to the blood outlet port, the blood flow path including first and second outlet blood flow paths within the outlet chamber via the first and second passageways, respectively, and further wherein the first and second outlet paths merge at the blood outlet port.

2. The apparatus of claim 1, wherein the housing includes an outer wall defining the primary chamber to have a generally cylindrical shape about the central longitudinal axis, and further wherein the outlet region includes an auxiliary wall extending from the outer side wall to define the outlet chamber.

3. The apparatus of claim 2, wherein the auxiliary wall locates the outlet chamber radially outward of the primary chamber.

4. The apparatus of claim 3, wherein the auxiliary wall includes an upper portion extending laterally outwardly from the side wall and a side portion extending from the upper portion, the side portion being radially spaced from the partition.

5. The apparatus of claim 4, wherein the blood outlet port extends from the side portion.

6. The apparatus of claim 4, wherein the partition extends from an intersection of the side wall and the upper portion.

7. The apparatus of claim 6, wherein a curvature of the partition corresponds with the curvature of the side wall.

8. The apparatus of claim 7, wherein relative to a circumference defined by an inner surface of the side wall, the partition circumferentially spaces the first and second passageways from one another.

9. The apparatus of claim 4, further comprising a floor body extending between the partition and the side portion, the floor body forming a boundary of the outlet chamber.

10. The apparatus of claim 9, wherein the floor body is a potting compound.

11. The apparatus of claim 1, wherein the first and second passageways are equidistant from the blood outlet port.

12. The apparatus of claim 1, further comprising a sampling port extending from, and fluidly open to, the blood outlet port, wherein the sampling port is radially outward of the outlet chamber.

13. The apparatus of claim 1, wherein the first passageway extends from a first opening at the partition and the second passageway extends from a second opening at the partition, and further wherein a plane perpendicular to the central longitudinal axis and passing through the blood outlet port intersects the first and second openings.

14. The apparatus of claim 12, further comprising a temperature monitoring probe port extending from, and fluidly open to, the blood outlet port.

15. The apparatus of claim 1, further comprising a heat exchanger core disposed within the primary chamber, wherein the oxygenator bundle is arranged about the heat exchanger core.

16. The apparatus of claim 1, wherein the housing further defines a de-aering chamber fluidly open to the primary chamber for receiving air bubbles from blood flowing through the primary chamber, the apparatus further comprising:
   an air purge line fluidly connected to the de-aering chamber; and
   a clamping mechanism associated with the air purge line for selectively opening and closing the air purge line.

17. The apparatus of claim 16, further comprising:
   an inlet line fluidly connected to the blood inlet port for delivering blood to the blood inlet port;
   a bubble detector associated with the inlet line for detecting the presence of air bubbles in the delivered blood; and
   a controller for controlling operation of the clamping mechanism as a function of information signaled by the bubble detector.

18. A method of operating an oxygenator apparatus for oxygenating blood within an extracorporeal circuit, the method comprising:
fluidly connecting a blood inlet port and a blood outlet port of an apparatus into an extracorporeal circuit, the apparatus including a housing forming a primary chamber fluidly open to the blood inlet port and an outlet region including an outlet chamber partially separated from the primary chamber by a partition, the blood outlet port being fluidly open to the outlet chamber, and an oxygenator bundle apart from the partition disposed within the primary chamber, wherein housing defines a central longitudinal, and further wherein relative to a plane perpendicular to the central longitudinal axis and passing through the primary chamber and the outlet chamber, the outlet chamber and the partition each surrounds less than an entirety of the primary chamber;
delivering blood from the patient to the blood inlet port; and
oxygenating the delivered blood as the delivered blood flows through the oxygenator bundle;
wherein the delivered blood flows from the inlet port, through the oxygenator bundle and to the blood outlet port, including the partition dividing blood flow from the oxygenator bundle into first and second blood outlet paths, the first and second paths merging at the blood outlet port.

19. The method of claim 18, wherein mixing of blood flow occurs along the first path.

20. The method of claim 19, further comprising obtaining a sample of the blood at the blood outlet port.

* * * * *